US00PP09061P

United States Patent [19]

Tobutt

[11] Patent Number: Plant 9,061

[45] Date of Patent: Feb. 21, 1995

[54] COLUMNAR APPLE TREE—HERCULES VARIETY

[75] Inventor: Kenneth R. Tobutt, Maidstone, United Kingdom

[73] Assignee: Horticulture Research International, Warwick, United Kingdom

[21] Appl. No.: 179,357

[22] Filed: Jan. 10, 1994

[51] Int. Cl.[6] ..... A01H 5/00

[52] U.S. Cl. ..... Plt./34.1

[58] Field of Search ..... Plt. 34.1, 34.2

[56] References Cited

PUBLICATIONS

Fogle, H. W., et al., "Apples" *North American and European Fruit and Tree Nut Germplasm Resources Inventory,* 1981, USDA, Misc. Pub. No. 1406, p. 52.

*Primary Examiner*—James R. Feyrer

*Attorney, Agent, or Firm*—Burns, Doane, Swecker & Mathis

[57] ABSTRACT

A new and distinct variety of apple tree is provided which exhibits a columnar growth habit that generally resembles a vertical pole. The growth habit is more compact than the previously released varieties of columnar apple trees. The new variety resulted from a cross between the WIJCIK variety (U.S. Plant Pat. No. 4,382) and the GREENSLEEVES variety (non-patented in the United States). Flowers form earlier than on the other varieties of columnar apple tres. The new variety forms attractive large light green fruit with a red flush. The fruit configuration is irregular, round and conical with a prominent knobby crown. The fruit flesh is cream colored. The harvest date typically is late September. The fruit can be cold-stored until March-April while present in an ambient atmosphere. The fruit stews and bakes well and has a crisp, tart, and sweet taste.

1 Drawing Sheet

SUMMARY OF THE INVENTION

The new variety of apple tree was created in the course of a planned plant breeding program that was initiated during 1975 at the East Malling Research Station of The Kent Incorporated Society for Promoting Experiments in Horticulture at East Malling, Maidstone, Kent, England. The female parent (i.e., the seed parent) was the WIJCIK variety (U.S. Plant Pat. No. 4,382) and the male parent (i.e., pollen parent) was the GREENSLEEVES variety (non-patented in the United States). The parentage of the new variety can be summarized as follows:

WIJCIK×GREENSLEEVES.

The seeds resulting from this pollination were sown and plants were obtained that were physically and biologically different from each other. Selective study resulted in the identification of a single plant of the new variety. The new variety of the present invention initially was designated SA 219/25.

It was found that the new apple variety of the present invention possesses the following combination of characteristics:

(a) exhibits a columnar growth habit that is more compact than that of previously available columnar apple varieties,
(b) flowers earlier than other previously available columnar apple varieties,
(c) forms attractive large light green fruit with a red flush possessing an irregular round conical configuration with a prominent knobby crown that can be cold-stored until approximately March–April while present in an ambient atmosphere, and
(d) commonly exhibits a late September harvest date.

The early flowering of the new variety in the United Kingdom generally corresponds to that of the IN- DARED and MCINTOSH RED varieties, and falls with Pollination Period No. 2.

The new variety is suited for culinary uses and stews and bakes well. The fruit commonly is crisp, tart, and sweet.

The columnar growth habit combined with extreme compactness is particularly striking. Side branches are very limited. When side branches occur, they can be readily removed with secateurs. The axillary buds tend to form on fruit-bearing spurs rather than extension shoots. The flowers and fruit tend to form along a single main branch or central leader (as illustrated). The distinctive growth habit of the new variety makes possible very dense planting. Rows of trees of the new variety form sturdy natural cordons. However, in extremely windy areas it may be desirable to at least partially shelter the trees from wind with appropriate wind barriers. The trees of the new variety are relatively easy to manage and require little pruning. It has been found that the pruning of the terminal bud does not induce typical branching. For instance, following such pruning 1 to 3 buds near the top of the remaining trunk commonly will break and will grow up vertically to replace the leader and a few shoots further down the tree may also form. Mechanized fruit picking can be employed if desired. The trunk commonly increases in girth sufficiently to allow the tree to bear an unthinned heavy crop of fruit. Additionally, the trees of the new variety can serve as space-saving pollinators in more conventional orchards. Alternatively, the trees of the new variety can be grown for ornamental purposes in parks, gardens, and along the roadside. The life expectancy of a tree of the new variety is believed to be at least 11 years.

The combination of characteristics exhibited by the new variety enables it to be readily distinguished from other columnar apply varieties, such as MAYPOLE (U.S. Plant Pat. No. 6,184), TELAMON (U.S. Plant Pat. No. 6,224), TUSCAN (U.S. Plant Pat. No. 6,225), TRAJAN (U.S. Plant Pat. No. 6,226), and OBELISK (U.S. Plant patent Ser. No. 179,312, filed concurrently herewith).

The new variety performs well on rootstocks such as MM106. The new variety further has been evaluated at the 1988 National Fruit Trials, Brogdale Farm, Faversham, Kent, England.

The new variety has been asexually reproduced at East Malling, Maidstone, Kent, England that has included budding on MM106 rootstock. The characteristics of the new variety have been found to be stable and to be capable of transmission through succeeding generations following such propagation.

No pest and disease resistance or susceptibility for the new variety has been noted to date.

The new variety has been named the HERCULES variety. In many countries the new variety is known as the CHARLOTTE variety.

BRIEF DESCRIPTION OF THE PHOTOGRAPHS

The accompanying photographs show as nearly true as it is reasonably possible to make the same in color illustrations of this character, typical specimens of the new variety while budded on MM106 rootstock. The photographs show plants being grow at East Malling, Maidstone, Kent, England. Color reference is made to the R.H.S. Colour Chart of The Royal Horticultural Society, London.

FIG. 1 illustrates three-year-old trees during April 1993. The highly compact columnar growth habit is apparent. Flowers borne on spurs arising directly from the main trunk are shown particularly on the middle tree. The production of an occasional short side-short is seen on the tree at the right. The illustrated flower petals generally are white with a touch of mauvy pink (Red-Purple Group 68D) on the upper side, and white striped with mauvy pink (Red-Purple Group 73C) on the under side.

FIG. 2 illustrates a cluster of fruit with foliage when observed during September 1992. The configuration of typical fruit generally is shown wherein the skin coloration of the fruit is light green with a red overcolor. Here a higher proportion of the fruit surface has developed the red overcolor than during the 1988 evaluation described hereafter where the red overcolor appeared over approximately 25 percent of the fruit surface.

DETAILED DESCRIPTION

Figure 1:
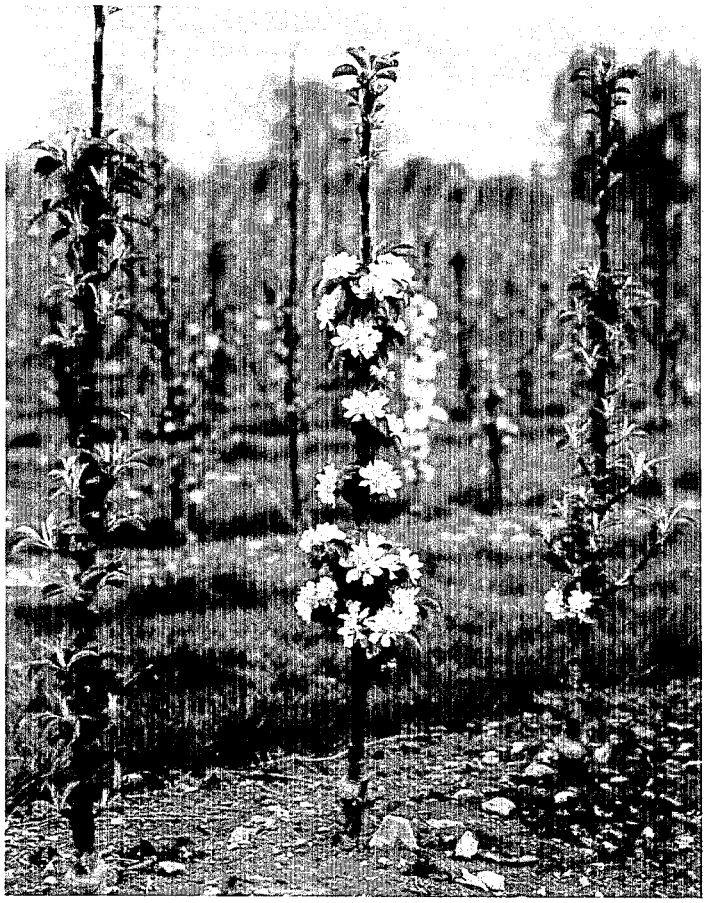
Figure 2:
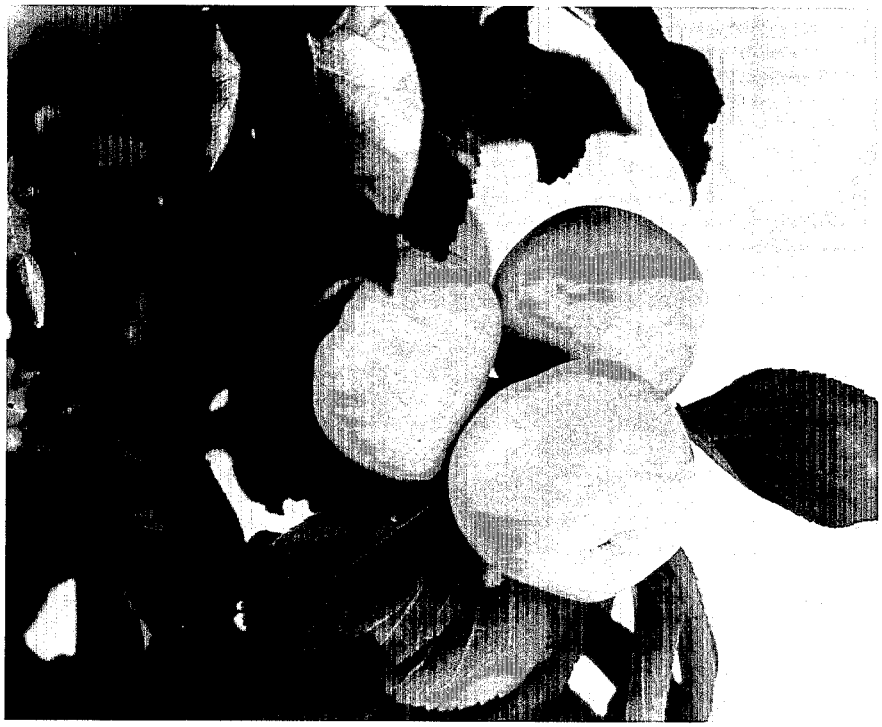

The following is a detailed description of the new CHARLOTTE apple variety. The specimens were grown during the 1988 National Fruit Trials in England while present on MM106 rootstock. Color reference is made to the R.H.S. Colour Chart of The Royal Horticultural Society, London.

Tree:

*Habit of branches.*—Columnar, a conventional branching system along the tree trunk is lacking, side branches rarely form, and commonly there is a central extension leader only. Approximately 10 internodes on average have been measured over a length of 10 cm. when observed at Cambridge, United Kingdom.

*Interspur length.*—Approximately 8 spurs on average have been measured over a length of 30 cm. when measured at Cambridge, United Kingdom.

*Bark.*—The current season's bark commonly is heavily pubescent and approaches Greyed-Green Group 197A in coloration, and the mature bark tends to be smooth and glossy and approaches Grey-Brown Group 199A in coloration.

*Bearing habit of tree.*—Spurs low on the tree develop and continue to bear fruit as the tree gains height, and there is some tendency for bare wood to be present on the lower portion of any extension shoots that form.

*Lenticel density on bark.*—Commonly averages approximately 11.2/cm$^2$ with the actual counts commonly ranging from 6 to 15/cm$^2$.

*Growth habit.*—Compact with extremely short internodes.

*Vigor.*—Weak.

*Dormant one year old shoot.*—Pubescence on the upper one-half of shoot is weak, the diameter at the center is thick, and many lenticels are present.

Leaves:

*Size.*—Very large and somewhat variable, approximately 109 mm in length on average and approximately 76 mm in width on average to provide a length to width ratio of approximately 1.4:1.

*General pose.*—Outwardly horizontal.

*Leaf blade.*—The ratio of the length to width is medium, and there is only weak glossiness on the upper end and under surfaces.

*Petiole.*—Long in length and commonly measures approximately 38 mm on average.

*Color.*—Upper surface approaches Yellow-Green Group 177A and lower surface approaches Yellow-Green Group 147C.

*Stipules.*—Present and commonly measure from approximately 1 to 2 cm. in length.

Flowers:

*Time of flowering.*—Earlier than other available columnar apple varieties in the United Kingdom, and approximately at the same time as the INDARED and MCINTOSH RED varieties at such location.

*Size.*—Medium, approximately 50 mm in diameter on average.

*Petals.*—Commonly are slightly overlapping, the upper side is white with small areas of mauvy pink (Red-Purple Group 68D) and the under side is white striped with mauvy pink (Red-Purple Group 73C).

*Pollen.*—Pollen is produced; however, the new variety is self-incompatible and requires pollen from another apple variety in order to set fruit.

Fruit:

*Predominance of bearing.*—On spurs.

*Size.*—Large (commonly of 70 to 100 mm in diameter). A mean value of 84.2 mm has been observed.

*Shape.*—Flat globose (oblate).

*Symmetry in side view.*—Somewhat asymmetric.

*Ribbing.*—Present with medium prominence.

*Crowning at distal end.*—Present to a medium degree.

*Aperture of eye.*—Open.

*Size of eye.*—Medium.

*Sepal length.*—Medium.

*Spacing of sepals at base.*—Free.

*Depth of eye basin.*—Deep to very deep, commonly approximately 15 mm on average.

*Width of eye basin.*—Medium broad.

*Thickness of stalk.*—Thick.

*Length of stalk.*—Short, commonly approximately 14 mm on average.

*Depth of stalk cavity.*—Medium, commonly approximately 12 mm on average.

*Width of stalk cavity.*—Broad, commonly approximately 32 mm on average.

*Relief of surface.*—Smooth.

*Bloom of skin.*—Absent.

*Greasiness of skin.*—Present.

*Cracking tendency of skin.*—Absent.

*Thickness of skin.*—Medium.

*Ground color of skin.*—Whitish green.

*Quantity of overcolor.*—Medium.

*Overcolor of skin.*—Red and somewhat banded (as illustrated).

*Quantity of russet.*—Absent or slight.

*Location of russet.*—Tends to be around stalk cavity if present.

*Size of lenticels.*—Medium.

*Browning of flesh (one hour after being cut with stainless steel knife).*—Weak.

*Firmness of flesh.*—Soft, and values averaging 3.3 have been observed using a penetrometer.

*Color of flesh.*—Cream.

*Texture of flesh.*—Fine.

*Grittiness.*—Absent.

*Juiciness.*—Medium.

*Distinctness of core line median through locules.*—Absent or very weak when the fruit is cut in cross-section.

*Aperture of locules.*—Was closed when the fruit is cut in cross-section at time of observation.

*Time of fruit ripening for eating.*—Medium, picking commonly takes place in late September in southeast England.

The new variety forms a culinary apple with a crisp, tart, sweet fruit. When cooked it melts down to a fluff and is suitable for stewing and baking uses in the preparation of applesauce and apple pies. In flavor it is reminiscent of BRAMLEY'S SEEDLING (non-patented in the United States) but is sweeter. The fruit of the new variety commonly can be cold-stored (e.g., at 4° C.) until March–April following harvest without any significant loss of eating quality.

I claim:

1. A new and distinct variety of apple tree having the following combination of characteristics:

(a) exhibits a columnar growth habit that is more compact than that of previously available columnar apple varieties, (b) flowers earlier than other previously available columnar apple varieties, (c) forms attractive large light green fruit with a red flush possessing an irregular round conical configuration with a prominent knobby crown that can be cold-stored until approximately March–April while present in an ambient atmosphere, and (d) commonly exhibits a late September harvest date;

substantially as herein shown and described.

* * * * *